United States Patent [19]
Hearn et al.

[11] Patent Number: 5,595,634
[45] Date of Patent: Jan. 21, 1997

[54] PROCESS FOR SELECTIVE HYDROGENATION OF HIGHLY UNSATURATED COMPOUNDS AND ISOMERIZATION OF OLEFINS IN HYDROCARBON STREAMS

[75] Inventors: Dennis Hearn; Gary R. Gildert; Hugh M. Putman, all of Pasadena, Tex.

[73] Assignee: Chemical Research & Licensing Company, Pasadena, Tex.

[21] Appl. No.: 500,101

[22] Filed: Jul. 10, 1995

[51] Int. Cl.⁶ .............................. B01D 3/34; C01G 7/00; C07C 5/22
[52] U.S. Cl. .............................. 203/29; 203/32; 203/33; 203/50; 203/71; 203/DIG. 6; 208/49; 208/92; 208/145; 208/217; 585/253; 585/260; 585/262; 585/264; 585/324; 585/809
[58] Field of Search .................... 203/29, 32, 33, 203/50, 71, 86, DIG. 6; 585/253, 260, 262, 264, 324, 809; 568/59; 208/49, 92, 145, 217

[56] References Cited

U.S. PATENT DOCUMENTS

| | | | |
|---|---|---|---|
| 2,493,499 | 1/1950 | Perry | 585/253 |
| 2,717,202 | 9/1955 | Bailey | 23/283 |
| 3,186,935 | 6/1965 | Vaell | 208/59 |
| 3,531,542 | 9/1970 | Myers et al. | 260/683.2 |
| 3,839,486 | 10/1974 | Arganbright | 260/683.2 |
| 4,213,847 | 7/1980 | Chen et al. | 208/111 |
| 4,221,653 | 9/1980 | Chervenak et al. | 208/8 LE |
| 4,232,177 | 11/1980 | Smith | 585/324 |
| 4,293,728 | 10/1981 | Montgomery | 585/670 |
| 4,361,422 | 11/1982 | Derrien et al. | 44/56 |
| 4,396,790 | 8/1983 | Ward | 585/664 |
| 4,404,124 | 9/1983 | Johnson et al. | 252/466 PT |
| 4,417,089 | 11/1983 | Drake | 585/670 |
| 4,439,350 | 3/1984 | Jones | 502/527 |
| 4,533,779 | 8/1985 | Boitiaux et al. | 585/259 |
| 4,724,274 | 2/1988 | Boitiaux et al. | 585/668 |
| 4,740,663 | 4/1988 | Boitiaux et al. | 568/699 |
| 5,012,021 | 4/1991 | Vora et al. | 585/315 |
| 5,087,780 | 2/1992 | Arganbright | 585/259 |
| 5,281,753 | 1/1994 | Olson et al. | 585/260 |
| 5,321,163 | 6/1994 | Hickey et al. | 568/59 |
| 5,431,888 | 7/1995 | Hickey et al. | 203/DIG. 6 |

OTHER PUBLICATIONS

Heck et al. Catalytic Process Using C4 Streams for Octane Improvement: Hydroisomerization and MTBE. American Chemical Society, Mar. 1980, pp. 38–50.
Boitiaux et al. Newest Hydrogenation Catalyst. Hydrocarbon Processing, Mar. 1985, pp. 51–59.

*Primary Examiner*—Robert J. Warden
*Assistant Examiner*—Robert Carpenter
*Attorney, Agent, or Firm*—Kenneth H. Johnson

[57] ABSTRACT

A process for treating $C_3$ to $C_{12}$ petroleum fractions, such as a light cracked naphtha to be used as an etherification feed stock in which $H_2S$ is removed by distillation of at least the $C_3$ fraction and mercaptans and diolefins are removed simultaneously in a distillation column reactor using a dual catalyst bed. The mercaptans and $H_2S$ are reacted with the diolefins in the presence of a reduced nickel catalyst to form sulfides which are higher boiling than the portion of the feed which is fractionated to an upper hydrogenation catalyst bed of palladium for hydrogenating diolefins and acetylenes. The higher boiling sulfides are removed as bottoms along with heavier materials. Any diolefins not converted to sulfides and acetylenes are selectively hydrogenated to monoolefins in the presence of a palladium oxide catalyst in an upper bed, producing overheads, substantially free of sulfur compounds, diolefins and acetylenes.

14 Claims, 1 Drawing Sheet

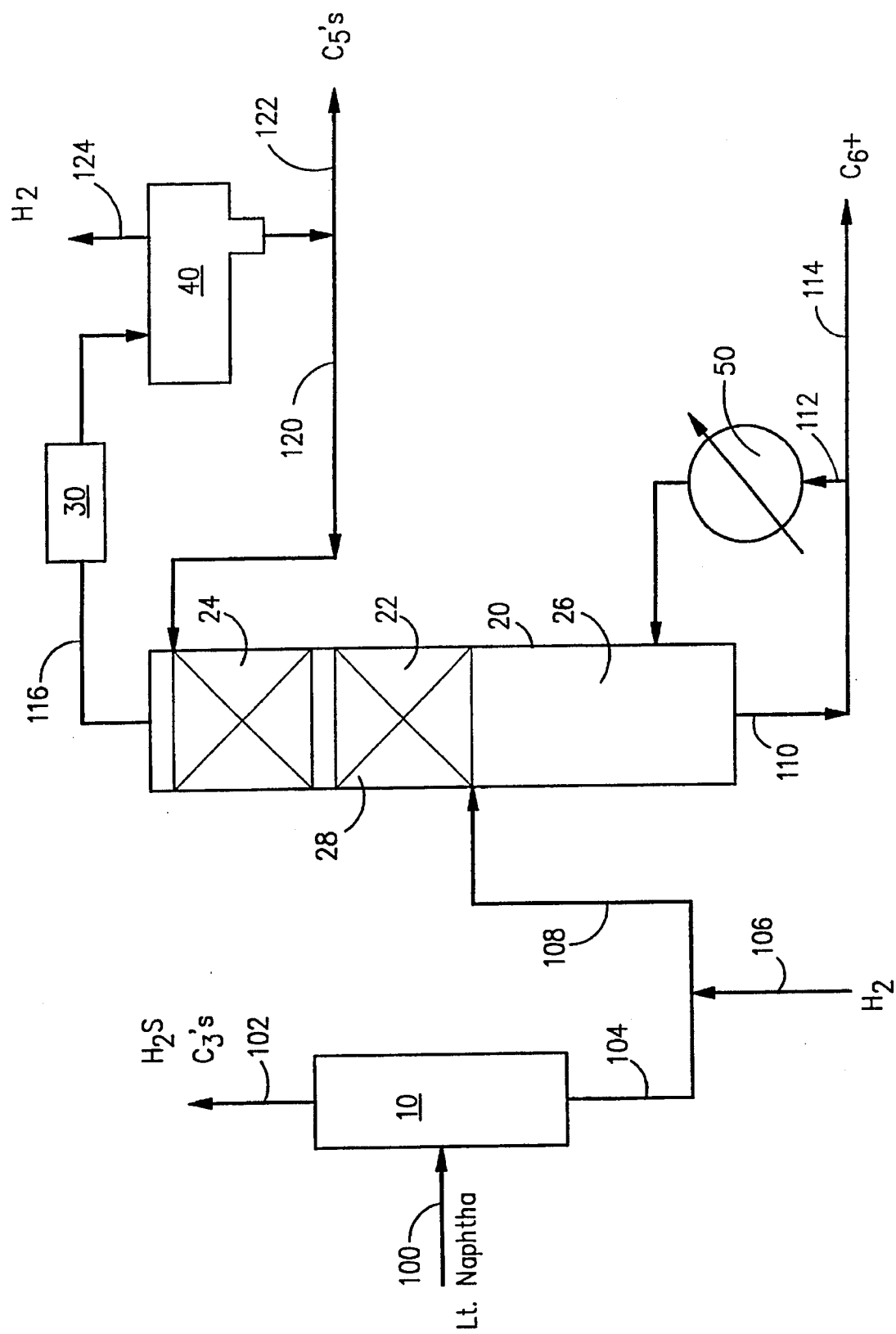

PROCESS FOR SELECTIVE HYDROGENATION OF HIGHLY UNSATURATED COMPOUNDS AND ISOMERIZATION OF OLEFINS IN HYDROCARBON STREAMS

BACKGROUND OF THE INVENTION

1. Field of the Invention

The present invention relates to the selective hydrogenation of diolefins and acetylenic compounds and isomerization of olefins to more desirable isomers in an olefin rich stream containing sulfur impurities. More particularly the invention relates to a process utilizing hydrogenation catalysts in a structure to serve as both the catalyst and as a distillation structure for the simultaneous reaction and separation of the reactants and reaction products.

The present process includes the removal of mercaptans, hydrogen sulfide ($H_2S$) and polyolefins from petroleum distillate streams. More particularly the invention relates to a process wherein the petroleum distillate contains diolefins which are selectively reacted with the mercaptans and/or hydrogen sulfide ($H_2S$) to form sulfides and the remaining diolefins and acetylenes are hydrogenated to mono-olefins. More particularly the invention relates to a process wherein the reaction of the mercaptans and/or hydrogen sulfide ($H_2S$) with the diolefins is carried out simultaneously with a fractional distillation to remove the sulfides, and thus the sulfur, from the distillate. Most particularly the invention relates to a process wherein most of the hydrogen sulfide is removed prior to the reaction of the diolefins and mercaptans.

2. Related Information

Petroleum distillate streams contain a variety of organic chemical components. Generally the streams are defined by their boiling ranges which determine the compositions. The processing of the streams also affects the composition. For instance, products from either catalytic cracking or thermal cracking processes contain high concentrations of olefinic materials as well as saturated (alkanes) materials and poly-unsaturated materials (diolefins). Additionally, these components may be any of the various isomers of the compounds.

The petroleum distillates often contain unwanted contaminants such as sulfur and nitrogen compounds. These contaminants often are catalyst poisons or produce undesirable products upon further processing. In particular the sulfur compounds can be troublesome. The sulfur compounds are known catalyst poisons for naphtha reforming catalysts and hydrogenation catalysts. The sulfur compounds present in a stream are dependent upon the boiling range of the distillate. In a light naphtha (110°–420° F. boiling range) the predominant sulfur compounds are mercaptans. Streams having $C_3$ hydrocarbons also may contain $H_2S$. The most common method for removal of the $H_2S$ is amine extraction and the most common method for removal of mercaptans is caustic washing of the organic streams.

Another method of removal of the sulfur compounds is by hydrodesulfurization (HDS) in which the petroleum distillate is passed over a solid particulate catalyst comprising a hydrogenation metal supported on an alumina base. Additionally copious quantities of hydrogen are included in the feed. The following equations illustrate the reactions in a typical HDS unit:

(1) $RSH+H_2 \rightarrow RH+H_2S$
(2) $RCl+H_2 \rightarrow RH+HCl$
(3) $2RN+4H_2 \rightarrow RH+NH_3$
(4) $ROOH+2H_2 \rightarrow RH+H_2O$ Typical operating conditions for the HDS reactions are:

| | |
|---|---|
| Temperature, °F. | 600–780 |
| Pressure, psig | 600–3000 |
| $H_2$ recycle rate, SCF/bbl | 1500–3000 |
| Fresh $H_2$ makeup, SCF/bbl | 700–1000 |

As may be seen the emphasis has been upon hydrogenating the sulfur and other contaminating compounds. The sulfur is then removed in the form of gaseous $H_2S$, which in itself is a pollutant and requires further treatment.

In addition to sulfur and nitrogen compounds mixed refinery streams contain a broad spectrum of olefinic compounds. This is especially true of products from either catalytic cracking or thermal cracking processes. These unsaturated compounds comprise ethylene, acetylene, propylene, propadiene, methyl acetylene, butenes, butadiene, amylenes, hexenes etc. Many of these compounds are valuable, especially as feed stocks for chemical products. Ethylene, especially is recovered. Additionally, propylene and the butenes are valuable. However, the olefins having more than one double bond and the acetylenic compounds (having a triple bond) have lesser uses and are detrimental to many of the chemical processes in which the single double bond compounds are used, for example polymerization. Over the range of hydrocarbons under consideration, the removal of highly unsaturated compounds is of value as a feed pretreatment, since these compounds have frequently been found to be detrimental in most processing, storage and use of the streams.

In the production of tertiary amyl methyl ether (TAME) for use as a gasoline additive generally a light cracked naphtha (LCN) is used as the source of the olefins for the etherification reaction. The acetylenes and diolefins are detrimental in the etherification process as well as in other processes such as alkylation and should be removed early in the stream processing. The LCN usually contains sulfur as a contaminant in the form of mercaptans in concentrations of up to hundreds wppm. These mercaptans are inhibitors for the hydrogenation catalyst used to hydrogenate dienes and acetylenes and obtain beneficial isomerization in the feed to an etherification unit or to an alkylation unit.

Although the most desirable hydrogenation catalysts are inhibited by sulfur compounds even in very small amounts, e.g. 10–100 ppm, there are other similar catalysts that will cause the sulfur compounds and the diolefins to form adducts, which can be separated from the lighter components.

It is an advantage of the present invention that the sulfur compounds can be separated from the lighter hydrocarbon components which can then be hydrotreated with the sulfur sensitive catalyst to hydrogenate highly unsaturated hydrocarbons and obtain beneficial isomerization of the mono-olefins. It is a particular advantage that this may be achieved in a single reactive distillation column by using beds of function specific catalyst. It is a particular feature of the present invention that a dual bed system may be used.

SUMMARY OF THE INVENTION

The present invention presents a new process for the removal of mercaptans and/or hydrogen sulfide ($H_2S$) from aliphatic hydrocarbon streams, containing 3 to 12 carbon atoms comprising distilling a hydrocarbon stream comprising $C_3$ to $C_{12}$ hydrocarbons including alkanes, mono-olefins, diolefins, acetylenes and minor amounts of sulfur compounds to remove a fraction comprising at least $C_3$'s and a portion of the sulfur compounds and leaving a residual, concurrently:

(1) feeding hydrogen and a portion of the residual to distillation column reactor containing a first bed comprising a first hydrogenation catalyst of the type characterized by nickel, cobalt or iron, preferably selected from nickel, cobalt, iron or mixtures thereof, and prepared in the form of a distillation structure and a second bed position in said column above said first bed, said second bed comprising a second hydrogenation catalyst of the type characterized by platinum, palladium or rhodium, preferably selected from platinum, palladium, rhodium or mixtures thereof, and prepared as a distillation structure wherein any sulfur compounds in the residual react in said first bed with a portion of the diolefins to form sulfides in a first reaction mixture, (2) fractionally distilling the first reaction mixture to remove the sulfides with a heavier fraction and passing a lighter fraction into the second bed (3) hydrogenating the diolefins and acetylenes in said second bed to form a second reaction mixture (4) fractionally distilling the second reaction mixture and (5) removing a fraction overhead, which is substantially free of sulfur compounds, acetylenes and diolefins.

In step 3 the hydrogenation of the more highly unsaturated compounds will produce more mono-olefins and/or alkanes. Also there may be bond shifting isomerization such as butene-2 to butene-1.

In the first (lower) bed the catalytic material may be initially present as the oxide or as reduced metal but is converted to the sulfide form during the reaction. Generally the catalytic material in the second (upper) bed is initially present as the metal oxide and may be converted to the hydride form during use by the hydrogen.

In the present invention hydrogen is provided at an effectuating hydrogen partial pressure of at least about 0.1 psia to less than 70 psia, preferably less than 50 psia, more preferably less than 35 psia to the distillation column reactor containing hydrogenation catalysts as described.

BRIEF DESCRIPTION OF THE DRAWING

The FIGURE is a flow diagram in schematic form of a preferred embodiment of the invention.

DESCRIPTION OF THE PREFERRED EMBODIMENTS

The present invention provides a process for the reaction of diolefins and acetylenes within a petroleum distillate with the mercaptans within the distillate to form sulfides and concurrent separation of the higher boiling sulfides from the distillate; selectively hydrogenating remaining diolefins and acetylenes and isomerizing the mono-olefins to equilibrium. This requires a distillation column reactor which contains at least two beds of an appropriate catalyst in the form of a catalytic distillation structure.

In the usual application of a process where the catalyst serves as a distillation component, the equilibrium is constantly disturbed, thus driving the reaction toward completion, that is, the reaction has an increased driving force because the reaction products have been removed and cannot contribute to a reverse reaction (LeChatelier's Principle). Although the hydrogenation reactions have been described as reversible at elevated temperatures above about 900° F., under the temperature conditions employed in the present invention, the hydrogenation is not reversible and cannot be an incentive to use a catalytic distillation system. The poor performance of prior vapor phase hydrogenations would not suggest the use of distillation type reaction.

It is believed that in the present reaction catalytic distillation is a benefit first, because the reaction is occurring concurrently with distillation, the initial reaction products and other stream components are removed from the reaction zone as quickly as possible reducing the likelihood of side reactions. Second, because all the components are boiling the temperature of reaction is controlled by the boiling point of the mixture at the system pressure. The heat of reaction simply creates more boil up, but no increase in temperature at a given pressure. As a result, a great deal of control over the rate of reaction and distribution of products can be achieved by regulating the system pressure. Also, adjusting the throughput (residence time=liquid hourly space velocity$^{-1}$) gives further control of product distribution and to a degree control of the side reactions such as oligomerization. A further benefit that this reaction may gain from catalytic distillation is the washing effect that the internal reflux provides to the catalyst thereby reducing polymer build up and coking. Internal reflux may be varied over the range of 0.2 to 20 L/D (wt. liquid just below the catalyst bed/wt. distillate) and gives excellent results, and with the $C_3$–$C_5$ streams being usually in the range of 0.5 to 4 L/D.

Quite surprisingly the low hydrogen partial pressure used in the distillation system did not result in the failure of the hydrogenation which would have been expected based on the high hydrogen partial pressure found in the liquid phase systems which are the worldwide standard. Without limiting the scope of the invention it is proposed that the mechanism that produces the effectiveness of the present process is the condensation of a portion of the vapors in the reaction system, which occludes sufficient hydrogen in the condensed liquid to obtain the requisite intimate contact between the hydrogen and the highly unsaturated compounds in the presence of the catalyst to result in their hydrogenation. This phenomenon of condensation which is a constant factor in a distillation is believed to result in the same or better hydrogen availability, as the high pressure in the liquid phase, that is, the hydrogen is introduced into the liquid so that the hydrogenation occurs.

The $C_5$'s in the feed to the present unit are contained in a single "light naphtha" cut which may contain everything from $C_3$'s through $C_8$'s and higher. This mixture can easily contain 150 to 200 components. Mixed refinery streams often contain a broad spectrum of olefinic compounds. This is especially true of products from either catalytic cracking or thermal cracking processes. Refinery streams are usually separated by fractional distillation, and because they often contain compounds that are very close in boiling points, such separations are not precise. A $C_5$ stream, for instance, may contain $C_3$'s and up to $C_8$'s. These components may be saturated (alkanes), unsaturated (mono-olefins), or polyunsaturated (diolefins). Additionally, the components may be any or all of the various isomers of the individual compounds. Such streams typically contain 15 to 30 weight % of the isoamylenes.

Such refinery streams also contain small amounts of sulfur which must be removed. The sulfur compounds are generally found in a light cracked naphtha stream as mercaptans and/or hydrogen sulfide ($H_2S$) which inhibit the hydrogenation catalyst used to selectively hydrogenate diolefins. Removal of sulfur compounds is generally termed "sweetening" a stream.

Several of the minor components (diolefins) in the feed will react slowly with oxygen during storage to produce "gum" and other undesirable materials. However, these components also react very rapidly in catalytic etherifications to form a yellow, foul smelling gummy material and consume acid in an alkylation unit. Thus it is seen to be desirable to remove these components whether the "light naphtha" cut is to be used only for gasoline blending by itself or as feed to a TAME (tertiary amyl methyl ether) or alkylation process.

Catalysts which are useful in all the reactions include the Group VIII metals. The preferred catalyst for the mercaptan-diolefin reaction (lower bed) is nickel. The preferred catalyst for the selective hydrogenation and isomerization (upper bed) is palladium. The palladium catalyst is inhibited by the presence of sulfur compounds and is thus placed above the nickel catalyst in the distillation column reactor such that the feed is first subjected to the nickel catalyst and the sulfur compounds removed by forming adducts with a portion of the diolefins in the feed. The catalyst may be use as individual Group VIII metal components or in admixture with each other or modifiers as known in the art, particularly those in Group VIB and IB.

Generally the metals are deposited as the oxides on an alumina support. The supports are usually small diameter extrudates or spheres, typically alumina. The catalyst must then be prepared in the form of a catalytic distillation structure. The catalytic distillation structure must be able to function as catalyst and as mass transfer medium. The catalyst must be suitably supported and spaced within the column to act as a catalytic distillation structure. In a preferred embodiment the catalyst is contained in a woven wire mesh structure as disclosed in U.S. Pat. No. 5,266,546 which is hereby incorporated by reference. Other catalytic distillation structures useful for this purpose are disclosed in U.S. Pat. Nos. 4,731,229, 5,073,236 and 5,431,890 which are also incorporated by reference.

In a preferred embodiment a light cracked stream which is used as a feed to an etherification or alkylation unit is the feed for this process. The light cracked naphtha contains $C_3$'s to $C_8$'s components which may be saturated (alkanes), unsaturated (olefins) and poly-unsaturated (diolefins) along with minor amounts of the mercaptans. The light naphtha is generally depentanized in a fractional distillation column to remove that portion containing the $C_6$ and higher boiling materials ($C_6+$) as bottoms and the $C_5$ and lower boiling materials ($C_5-$) as overheads.

In the present invention the stream is first subjected to a distillation in a distillation vessel wherein the $C_3$'s, $H_2S$ and a portion of the $C_4$'s are distilled overhead. The $C_3$'s overheads may be subjected to the traditional amine extraction to remove the $H_2S$. The bottoms from the distillation ($C_4+$) are fed to a debutanizer or depentanizer which has two separate distillation reaction beds in the rectification section.

The lower bed contains a nickel sulfide catalytic distillation component to first react substantially all of the mercaptans (and residual $H_2S$) contained in the light cracked naphtha with a portion of the diolefins to form sulfides which are higher boiling than the $C_5$ fraction containing the amylenes which are fed to the etherification and/or alkylation unit. The sulfides are removed as bottoms from the depentanizer along with the $C_6+$ fraction and can be remixed into the final gasoline fraction.

The upper bed contains a supported palladium catalytic distillation structure which selectively hydrogenates the remainder of the diolefins while at the same time isomerizing the mono-olefins to equilibrium.

Hydrogen is provided as necessary to support the reaction. The distillation column reactor is operated at a pressure such that the reaction mixture is boiling in the bed of catalyst. A "froth level", as described in U.S. Pat. No. 5,221,441 which is incorporated herein, may be maintained throughout the catalyst bed by control of the bottoms and/or overheads withdrawal rate, although the preferred operation is without the froth. As may be appreciated in the froth mode the liquid is boiling and the physical state is actually a froth having a higher density than would be normal in a packed distillation column but less than the liquid without the boiling vapors.

The present process preferably operates at overhead pressure of said distillation column reactor in the range between 0 and 250 psig and temperatures within said distillation reaction zone in the range of 100° to 300° F., preferably 130° to 270° F.

The feed and the hydrogen are preferably fed to the distillation column reactor separately or they may be mixed prior to feeding. A mixed feed is fed below the lower catalyst bed or at the lower end of the bed. Hydrogen alone is fed below the catalyst bed and the hydrocarbon stream is fed below the first bed to about the mid one-third of the first bed. The pressure selected is that which maintains catalyst bed temperature between 100° F. and 300° F.

A preferred catalyst for the mercaptan-diolefin reaction is 54 wt % Ni on 8 to 14 mesh alumina spheres, supplied by Calcicat, designated as E-475-SR. Typical physical and chemical properties of the catalyst as provided by the manufacturer are as follows:

TABLE I

| Designation | E-475-SR |
|---|---|
| Form | Spheres |
| Nominal size | 8 × 14 Mesh |
| Ni wt % | 54 |
| Support | Alumina |

A preferred catalyst for the selective hydrogenation/isomerization reactions is palladium oxide, preferably 0.1 to 5.0 weight %, supported on an appropriate support medium such as alumina, carbon or silica, e.g., ⅛" alumina extrudates. The catalyst used is 0.4 wt % Pd on ⅛" $Al_2O_3$ (alumina) extrudates, hydrogenation catalyst, supplied by United Catalysts, Inc. designated as G68C-1. Typical physical and chemical properties of the catalyst as provided by the manufacturer are as follows:

TABLE II

| Designation | G68C-1 |
|---|---|
| Form | spheres |
| Nominal size | 8 × 12 Mesh |
| Pd. wt % | 0.4 |
| Support | High purity alumina |

The hydrogen rate to the distillation column reactor must be sufficient to maintain the reaction, but kept below that which would cause flooding of the column which is understood to be the "effectuating amount of hydrogen" as that term is used herein. Generally the mole ratio of hydrogen to diolefins and acetylenes in the feed is at least 1.0 to 1.0, preferably at least 2.0 to 1.0 and more preferably at least 10 to 1.0.

The nickel catalyst also catalyzes the selective hydrogenation of the diolefins contained within the light cracked naphtha and to a lesser degree the isomerization of some of the mono-olefins. However, the palladium catalyst is preferred for these reactions. Generally the relative absorption preference is as follows:

(1) sulfur compounds
(2) diolefins
(3) mono-olefins

If the catalyst sites are occupied by a more strongly absorbed species, reaction of these weaker absorbed species cannot occur. For this reason the sulfur compounds are removed utilizing the nickel catalyst.

The reaction of interest in the nickel catalyst bed is the reaction of the mercaptans and, to a lesser extent hydrogen sulfide ($H_2S$) with diolefins. The equation of interest which describes the reaction is:

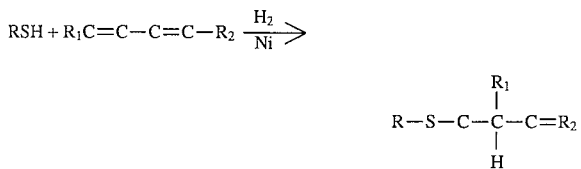

Where R, $R_1$ and $R_2$ are independently selected from hydrogen and hydrocarbyl groups of 1 to 20 carbon atoms. If there is concurrent hydrogenation of the dienes, then hydrogen will be consumed in that reaction.

Typical of the mercaptan compounds which may be found to a greater or lesser degree in a light cracked naphtha are: methyl mercaptan (b.p. 43° F.), ethyl mercaptan (b.p. 99° F.), n-propyl mercaptan (b.p. 154° F.), iso-propyl mercaptan (b.p. 135°–140° F.), iso-butyl mercaptan (b.p. 190° F.), tert-butyl mercaptan (b.p. 147° F.), n-butyl mercaptan (b.p. 208° F.), sec-butyl mercaptan (b.p. 203° F.), iso-amyl mercaptan (b.p. 250° F.), n-amyl mercaptan (b.p. 259° F.), α-methylbutyl mercaptan (b.p. 234° F.), α-ethylpropyl mercaptan (b.p. 293° F.), n-hexyl mercaptan (b.p. 304° F.), 2-mercapto hexane (b.p. 284° F.), and 3-mercapto hexane (b.p. 135° F. at 20 mm Hg). The reaction of $H_2S$ with the diolefins has been found to be considerably slower than the other sulfides and thus the preferred process removes the $H_2S$ prior to subjecting the feed to the two catalyst beds.

The reactions of the $C_4$'s of interest are:
(1) butadiene-1,3+hydrogen to butene-1 and butene-2 and
(2) butene-2 to butene-1.

The reactions of the $C_5$'s of interest are:
(1) isoprene (2-methyl butadiene-1,3)+hydrogen to 2-methyl butene-1, 2-methyl butene-2 and 3-methyl butene-1;
(2) cis- and trans 1,3-pentadienes (cis and trans piperylenes)+hydrogen to pentene-1 and pentene-2;
(3) 3-methyl butene-1 to 2-methyl butene-2 and 2-methyl butene-1;
(4) 2-methyl butene-1 to 2-methyl butene-2; and
(5) 2-methyl butene-2 to 2-methyl butene-1.

The first two $C_5$ reactions remove the undesirable components while the third is advantageous for feed to a TAME reactor. The 3-methyl butene-1 does not react with methanol to produce TAME over the sulfonic acid catalyst while the two 2-methyl butenes do.

The present invention carries out the method in a catalyst packed column which can be appreciated to contain a vapor phase and some liquid phase as in any distillation. The distillation column reactor is operated at a pressure such that the reaction mixture is boiling in the bed of catalyst. The present process operates at overhead pressure of said distillation column reactor in the range between 0 and 350 psig, preferably 250 or less and temperatures within said distillation reaction zone in the range of 40° to 300° F., preferably 110° to 270° F. at the requisite hydrogen partial pressures. The feed weight hourly space velocity (WHSV), which is herein understood to mean the unit weight of feed per hour entering the reaction distillation column per unit weight of catalyst in the catalytic distillation structures, may vary over a very wide range within the other condition perimeters, e.g. 0.5 to 35.

The advantages of utilizing a distillation column reactor in the instant selective hydrogenation process lie in the better selectivity of diolefin to olefin, conservation of heat and the separation by distillation which can remove some undesirable compounds, e.g. the sulfur contaminants, from the feed prior to exposure to the hydrogenation/isomerization catalyst (the sulfides which are produced in the lower nickel catalyst bed are higher boiling than the $C_4$'s and $C_5$'s so are distilled downward in the column away from the upper palladium catalyst bed) and the distillation can concentrate desired components in the catalyst zone.

The temperature in the distillation column reactor is determined by the boiling point of the liquid mixture present at any given pressure. The temperature in the lower portions of the column will reflect the constitution of the material in that part of the column, which will be higher than the overhead; that is, at constant pressure a change in the temperature of the system indicates a change in the composition in the column. To change the temperature the pressure is changed. Temperature control in the reaction zone is thus effected by a change in pressure; by increasing the pressure, the temperature in the system is increased, and vice versa.

Referring now to the FIGURE there is depicted a simplified flow diagram of one embodiment of the invention. The combined $C_3$-naphtha stream containing the olefins, diolefins, mercaptans, and $H_2S$ is first fed via flow line 100 to a distillation column 10 where the $C_3$'s and substantially all of the $H_2S$ is distilled overhead and removed via flow line 102 for further sweetening as necessary. Generally a portion of the $C_4$'s must be included in the overheads to insure that essentially all of the $H_2S$ is removed. The bottoms from the distillation column 10 are removed via flow line 104 and combined with hydrogen from flow line 106 into combined feed line 108 and fed to the distillation column reactor 20. In this embodiment the $C_4$'s are removed with the $C_3$'s in the distillation column.

Distillation column reactor 20 is shown to have a stripping section 26 in the lower half and a rectifying section 28 in the upper half. Two catalyst beds are disposed in the rectifying section. The lower catalyst bed 22 contains the nickel sulfide catalyst in the form of a catalytic distillation structure for the mercaptan-diolefin reaction and the upper catalyst bed 24 contains the palladium oxide in the form of a catalytic distillation structure for the selective hydrogenation/isomerization reactions.

The combined feed stream in flow line 108 is fed into the distillation column reactor directly below the lower bed. The $C_6$+ material is separated from the $C_5$ and lighter material in the stripping section 26 with the $C_5$ and lighter material boiling up into the first catalyst bed where the diolefins react with substantially all of the mercaptans to form higher boiling sulfides. The sulfides are distilled back down the column into the stripping section where they are removed as bottoms with the $C_6$+ heavier material via flow line 110. A portion of the bottoms may be circulated through reboiler 50 via flow line 112 to provide heat balance to the column. The remainder of the bottoms are taken as product via flow line 114.

The substantially sulfur free C₅ and lighter material is then boiled upward into the upper bed 24 of the rectifying section where the material is contacted with hydrogen in the presence of the palladium catalyst. The remaining diolefins and acetylenes are selectively hydrogenated to mono-olefins and the mono-olefins are isomerized to equilibrium.

The $C_5$ and lighter distillate ($C_5-$), less the mercaptans, diolefins and acetylenes and having an increased percentage of 2-methyl-butene-1 and 2-methyl-butene-2 are removed as overheads via flow line 116 and passed through condenser 30 where the condensible materials are condensed. The liquids are collected in accumulator 40 where the gaseous materials, including any unreacted hydrogen, are separated and removed via flow line 124. The unreacted hydrogen may be recycled (not shown) if desired. The liquid distillate product is removed via flow line 122. Some of the liquid is recycled to the column 20 as reflux via line 120.

Generally the $C_5$ and lighter material will be used as feed stock for a etherification unit where the isoamylenes contained therein will be converted to TAME or tertiary amyl ethyl ether (TAEE). This TAME or TAEE is recombined with the $C_6$ bottoms and sent to gasoline blending. If desired the bottoms can be subjected to destructive hydrodesulfurization to remove the sulfides and other heavier sulfur compounds.

In another embodiment a light cracked naphtha as described is distilled to remove $C_3$'s and $H_2S$, with $C_4$'s and heavier going as bottoms from the distillation column to a first distillation column reactor containing a dual bed hydrogenation catalyst, where the $C_5$'s and heavier are taken as bottoms and the $C_4$'s as overheads after contacting the catalysts in the beds with hydrogen. The bottoms may be further treated in a second distillation column reactor with a hydrogenation catalyst and hydrogen to treat the $C_5$ portion which is recovered as the overheads from the second distillation column reactor and the $C_6$ and heavier as bottoms. In another embodiment the $C_4$'s and $C_5$'s are taken as the overheads in the first distillation column reactor and the $C_6$'s and heavier as bottoms.

EXAMPLES

In the Examples a three inch diameter column is loaded with 35 feet of the palladium catalyst as distillation structure in the upper portion of the column. Below the first catalyst 13.3 feet of the nickel catalyst was loaded. A stripping section of 50 feet containing Pall rings was left below the lower nickel catalyst bed.

In Example 1 the feed to the reaction distillation column was a $C_5+$ naphtha with the $C_3/H_2S/C_4$ removed in the distillation column, with the $C_5$'s being taken as overheads after contact with the dual beds. In Example 2 the naphtha cut is $C_4+$, with $C_4/C_5$ being contacted with the dual beds and being taken as overheads. In both examples the bottoms are $C_6+$. The conditions and results are shown in TABLE III below. The chromatographic analysis of the overheads was conducted for undersirables. In both runs the sulfur (mercaptan) reduction was essentially complete and dienes were reduced over 99.8%.

TABLE III

| EXAMPLE | 1 | 2 |
|---|---|---|
| Conditions | | |
| Pressure, psig | 130 | 130 |
| H₂ partial press. psia | 6.00 | 3.35 |
| Temperature, °F. | | |
| ovhd | 226 | 219.9 |
| top bed | 226 | 226 |
| lower bed | 245 | 245 |
| Flow rates, lbs/hr | | |
| feed | 219.9 | 219.9 |
| ovhd | 56.5 | 56.5 |
| mdrflx | 135.0 | 135 |
| H₂ rate, scfh | 40.0 | 40 |
| Feed Analysis | | |
| total C₄'s, wt % | | 7.67 |
| C₄ dienes, wt % of C₄'s | | 0.97 |
| butenes, wt % of C₄'s | | 53.85 |
| total C₅'s, wt % | 26.4 | 16.4 |
| dienes wt % of C₅'s | 1.99 | 1.99 |
| n-pentenes, wt % of C₅'s | 29.92 | 29.29 |
| isoamylenes, wt % of C5's | 34.65 | 34.65 |
| Pentene-1:n-pentene % | 19.0 | 19.0 |
| 3MB1:IA, % | 4.7 | 4.7 |
| EtSH in C₅'s (Sulfur), wppm | 51 | 51 |
| MeSH in feed, wppm | | 36 |
| Overheads Analysis | | |
| Dienes, wt % | 0.0046 | 0.0046 |
| 1,3-BD | | 0.000 |
| EtSH, (Sulfur), wppm | 0 | 0 |
| MeSH, wppm | | 0 |
| Pentene-1:n-pentene | 5.3 | 5.3 |
| 3MB1:IA | 1.2 | 1.2 |

The invention claimed is:

1. A process for the removal of mercaptans and/or hydrogen sulfide from aliphatic hydrocarbon streams, containing 3 to 12 carbon atoms comprising distilling a hydrocarbon stream comprising $C_3$ to $C_{12}$ hydrocarbons including alkanes, mono-olefins, diolefins, acetylenes and sulfur compounds to remove a fraction comprising at least $C_3$'s and a portion of the sulfur compounds and leaving a residual, concurrently (a) feeding hydrogen and a portion of the residual to a distillation column reactor containing a first bed comprising a first hydrogenation catalyst selected from the group consisting of nickel, cobalt, iron and compounds thereof and prepared in the form of a distillation structure and a second bed positioned in said column above said first bed, said second bed comprising a second hydrogenation catalyst selected from the group consisting of platinum, palladium, rhodium and the compounds thereof and prepared as a distillation structure wherein any sulfur compounds in the residual react in said first bed with a portion of the diolefins to form sulfides in a first reaction mixture, (b) fractionally distilling the first reaction mixture to remove the sulfides with a heavier fraction and passing a lighter fraction into the second bed, (c) hydrogenating the diolefins and acetylenes in said lighter fraction in said second bed to form a second reaction mixture, (d) fractionally distilling the second reaction mixture, and (e) removing a fraction overhead, which is substantially free of sulfur compounds, acetylenes and diolefins.

2. The process according to claim 1 wherein said second hydrogenation catalyst comprises palladium.

3. The process according to claim 1 wherein said first hydrogenation catalyst comprises nickel.

4. The process according to claim 1 wherein the hydrogen partial pressure within said distillation column reactor is between 0.1 and 75 psia.

5. A process for removing mercaptans and hydrogen sulfide from a hydrocarbon stream and for selectively hydrogenating the diolefins and acetylenes therein while isomerizing the mono-olefins to equilibrium, comprising the steps of:

(a) feeding a $C_3$ and heavier hydrocarbon stream containing hydrogen sulfide, mercaptans, olefins, diolefins and acetylene to a distillation column where the $C_3$'s and hydrogen sulfide are removed as overheads and the remainder of the stream is removed as bottoms;

(b) feeding said bottoms and hydrogen to a distillation column reactor and concurrently therein:

(1) separating the $C_5$ and lighter hydrocarbons and mercaptans from the $C_6$ and heavier hydrocarbons in a stripping section;

(2) distilling the $C_5$ and lighter hydrocarbons along with the mercaptans upwards into a first distillation reaction zone containing a supported nickel sulfide catalyst in the form of a catalytic distillation structure whereby a portion of the mercaptans react with a portion of the diolefins to form higher boiling sulfides which are distilled downward into said stripping section;

(3) distilling the $C_5$ and lighter hydrocarbons, less said reacted mercaptans and diolefins, upward into a second distillation reaction zone containing a supported palladium oxide catalyst in the form of a catalytic distillation structure whereby a portion of the remaining diolefins and acetylenes are selectively hydrogenated to mono-olefins and a portion of the mono-olefins are isomerized;

(c) removing said hydrogenated and isomerized $C_5$ and lighter hydrocarbons along with unreacted hydrogen as overheads from said distillation column reactor; and (d) removing said $C_6$ and heavier hydrocarbons and said sulfides from said distillation column reactor as bottoms.

6. The process according to claim 5 wherein the unreacted hydrogen is separated from said overheads and recycled to said distillation column reactor.

7. The process according to claim 5 wherein the pressure within said distillation column reactor is between 0 and 350 psig.

8. The process according to claim 7 wherein $C_4$'s are distilled overhead in step (a) leaving bottoms comprising substantially $C_5$ and heavier.

9. The process according to claim 5 wherein the hydrogen partial pressure within said distillation column reactor is between 0.1 and 75 psia.

10. The process according to claim 7 wherein substantially all of said hydrogen sulfide is removed with the overheads from said distillation column.

11. The process according to claim 5 wherein substantially all of said mercaptans react with diolefins to form sulfides.

12. The process according to claim 5 wherein substantially all of said remaining diolefins and acetylenes are selectively hydrogenated to mono-olefins.

13. The process according to claim 5 wherein said mono-olefins are isomerized to equilibrium in said upper distillation reaction zone.

14. A process for removing mercaptans and hydrogen sulfide from a hydrocarbon stream and for selectively hydrogenating the diolefins and acetylenes therein while isomerizing the mono-olefins to equilibrium, comprising the steps of:

(a) feeding a $C_3$ and heavier hydrocarbon stream containing hydrogen sulfide, mercaptans, olefins, diolefins and acetylene to a distillation column where substantially all of the $C_3$'s, substantially all of the hydrogen sulfide and a portion of the $C_4$'s are removed as overheads and the remainder of the stream is removed as bottoms;

(b) feeding said bottoms and hydrogen to a distillation column reactor and concurrently therein:

(1) separating the $C_5$ and lighter hydrocarbons and mercaptans from the $C_6$ and heavier hydrocarbons in a stripping section;

(2) distilling the $C_5$ and lighter hydrocarbons along with the mercaptans upwards into a first distillation reaction zone containing a supported nickel sulfide catalyst in the form of a catalytic distillation structure whereby substantially all of the mercaptans react with a portion of the diolefins to form higher boiling sulfides which are distilled downward into said stripping section;

(3) distilling the $C_5$ and lighter hydrocarbons less said portion of the mercaptans and said portion of diolefins upward into a second distillation reaction zone containing a supported palladium oxide catalyst in the form of a catalytic distillation structure whereby substantially all of the remaining diolefins and acetylenes are selectively hydrogenated to mono-olefins and a portion of the mono-olefins is isomerized;

(c) removing said hydrogenated and isomerized $C_5$ and lighter hydrocarbons along with unreacted hydrogen as overheads from said distillation column reactor; and (d) removing said $C_6$ and heavier hydrocarbons and said sulfides from said distillation column reactor as bottoms.

* * * * *